(12) United States Patent
Ellington et al.

(10) Patent No.: US 8,298,764 B2
(45) Date of Patent: Oct. 30, 2012

(54) SELECTION METHOD FOR CELL INTERNALIZING NUCLEIC ACIDS

(75) Inventors: Andrew D. Ellington, Austin, TX (US); Matthew Levy, Larchmont, NY (US); Amy Yan, Larchmont, NY (US); Ted Chitai Chu, Palo Alto, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 183 days.

(21) Appl. No.: 12/100,390

(22) Filed: Apr. 9, 2008

(65) Prior Publication Data

US 2009/0170711 A1    Jul. 2, 2009

Related U.S. Application Data

(60) Provisional application No. 60/910,792, filed on Apr. 9, 2007, provisional application No. 60/984,656, filed on Nov. 1, 2007.

(51) Int. Cl.
*C12Q 1/68* (2006.01)
*C12N 5/00* (2006.01)
*C12N 5/02* (2006.01)
*C07H 21/02* (2006.01)

(52) U.S. Cl. .......... 435/6.1; 435/325; 536/23.1

(58) Field of Classification Search .......... None
See application file for complete search history.

(56) References Cited

U.S. PATENT DOCUMENTS

| | | | | |
|---|---|---|---|---|
| 2005/0256071 A1* | 11/2005 | Davis | | 514/44 |
| 2006/0105975 A1* | 5/2006 | Pendergrast et al. | | 514/44 |
| 2007/0041901 A1* | 2/2007 | Diener et al. | | 424/1.49 |
| 2007/0140970 A1* | 6/2007 | Martin et al. | | 424/9.6 |

OTHER PUBLICATIONS

Zhang et al., Uptake, cellular distribution and novel cellular binding proteins of immunostimulatory CpG oligodeoxynucleotides in glioblastoma cells, 2005, Molecular and Cellular Biochemistry, vol. 272, pp. 35-46.*
International Search Report and Written Opinion for PCT/US2008/059805 dated Jul. 9, 2008.
Chrzanowska-Lightowlers, et al., "Fending off decay: a combinatorial approach in intact cells for identifying mRNA stability elements," RNA (2001), 7:435-444.
Chu, et al., "Aptamer: Toxin Conjugates that Specifically Target Prostate Tumor Cells," Cancer Res (2006), 66:5989-5992.
Gotte, et al., "Biglycan is internalized via a chlorpromazine-sensitive route," Cell Mol Biol Lett (2004), 9:475-481.
Hannon, et al., "Unlocking the potential of the human genome with RNA interference," Nature (2004), 431:371-378.
Chu et al., Aptamer medicated siRNA delivery, Nuliec Acids Res. Jun. 1, 2006;34(10):e73.
Farokhzad, et al., "Targeted nanoparticle-aptamer bioconjugates for cancer chemotherapy in vivo," PNAS (2006), 103:6315-6320.
Lupold, et al., "Identification and Characterization of Nuclease-stabilized RNA Molecules That Bind Human Prostate Cancer Cells via the Prostate-specific Membrane Antigen," Cancer Res. (2002), 62: 4029-33.
McNamara, II, et al., "Cell type-specific delivery of siRNAs with aptamer siRNA chimeras," Nat Biotech (2006), 24:1005-1015.
Wu, et al., "Selection of Oligonucleotide Aptamers with Enhanced Uptake and Activation of Human Leukemia B Cells," Human Gene Ther (2003), 14:849-860.
Brieba, Luis G., et al., "Roles of Histidine 784 and Tyrosine 639 in Ribose Discrimination by T7 RNA Polymerase," Biochemistry (2000) 39:919-923.

* cited by examiner

*Primary Examiner* — Dana Shin
(74) *Attorney, Agent, or Firm* — Edwin S. Flores; Chainey P. Singleton; Chalker Flores, LLP (57) ABSTRACT

The present invention includes compositions and methods for contacting one or more cells with a random RNA-containing library, treating the contacted cells and with a denaturing agent or digestion with one or more nucleases, and extracting from the cells one or more internalized nucleic acids resistant to the nucleases or denaturants.

22 Claims, 3 Drawing Sheets

SEQUENCE LISTING

```
<160> NUMBER OF SEQ ID NOS: 6

<210> SEQ ID NO 1
<211> LENGTH: 80
<212> TYPE: DNA
<213> ORGANISM: Artificial
<220> FEATURE:
<223> OTHER INFORMATION: Chemically Synthesized Oligonucleotides
<220> FEATURE:
<221> NAME/KEY: misc_feature
<222> LOCATION: (27)..(56)
<223> OTHER INFORMATION: n is any base A, T, C or G

<400> SEQUENCE: 1
gggaatggat ccacatctac gaattcnnnn nnnnnnnnnn nnnnnnnnnn nnnnnnttca     60
ctgcagactt gacgaagctt                                                80

<210> SEQ ID NO 2
<211> LENGTH: 41
<212> TYPE: DNA
<213> ORGANISM: Artificial
<220> FEATURE:
<223> OTHER INFORMATION: Chemically Synthesized Oligonucleotides

<400> SEQUENCE: 2
gataatacga ctcactatag ggaatggatc cacatctacg a                        41

<210> SEQ ID NO 3
<211> LENGTH: 24
<212> TYPE: DNA
<213> ORGANISM: Artificial
<220> FEATURE:
<223> OTHER INFORMATION: Chemically Synthesized Oligonucleotides

<400> SEQUENCE: 3
aagcttcgtc aagtctgcag tgaa                                           24

<210> SEQ ID NO 4
<211> LENGTH: 70
<212> TYPE: RNA
<213> ORGANISM: Artificial
<220> FEATURE:
<223> OTHER INFORMATION: Chemically Synthesized Oligonucleotides

<400> SEQUENCE: 4
gggaggacga ugcggaccga aaaagaccug acuucuauac uaagucuacg uucccagacg     60
acucgcccga                                                           70

<210> SEQ ID NO 5
<211> LENGTH: 35
```

```
<212> TYPE: DNA
<213> ORGANISM: Artificial
<220> FEATURE:
<223> OTHER INFORMATION: Chemically Synthesized Oligonucleotides

<400> SEQUENCE: 5
ttctaatacg actcactata gggaggacga tgcgg                              35

<210> SEQ ID NO 6
<211> LENGTH: 16
<212> TYPE: DNA
<213> ORGANISM: Artificial
<220> FEATURE:
<223> OTHER INFORMATION: Chemically Synthesized Oligonucleotides

<400> SEQUENCE: 6
tcgggcgagt cgtctg                                                   16
```

SELECTION METHOD FOR CELL INTERNALIZING NUCLEIC ACIDS

CROSS-REFERENCE TO RELATED APPLICATIONS

This application claims priority to U.S. Provisional Application Ser. No. 60/910,792, filed Apr. 9, 2007 and 60/984,656, filed Nov. 1, 2007, the entire contents of each are incorporated herein by reference.

FIELD OF THE INVENTION

The present invention relates in general to the fields of molecular biology and biochemistry. More specifically, the invention relates to nucleic acid targeting, and to methods, compositions, and kits for the selection and delivery of RNA-containing molecules.

STATEMENT OF FEDERALLY FUNDED RESEARCH

None.

BACKGROUND OF THE INVENTION

Currently, the delivery of agents into cells requires coordinated delivery mechanisms that are often toxic, inefficient or highly non-specific. Furthermore, many agents delivered into cells are toxic, and require specific and rapid internalization to the appropriate cell to prevent undesired toxicity to the organism.

SUMMARY OF THE INVENTION

A need exists for the identification and selection of compounds that can deliver agents into cells with reduced toxicity and non-specific effects on the organism. In addition, the need exists for methods of selecting compounds that can rapidly internalize agents to a predetermined tissue, cell, or group of cells.

By analyzing mechanisms of cellular internalization, it has been discovered that certain classes of molecules can deliver molecular cargo into the cell. This discovery has been exploited to provide methods that allow for the selection, optimization, and/or modification of such molecules for cell internalization and molecular cargo delivery. According to some aspects, certain methods also allow for the identification of the most rapidly internalized molecules.

In one aspect, a method for selecting nuclease-resistant— and in certain embodiments, stabilized—RNA-containing molecules is provided. The method comprises contacting a cell (e.g., a eukaryotic or prokaryotic cell) with a random library of RNA-containing molecules. The cells that are contacted with the random library are then exposed to one or more nucleases. Total RNA is then extracted from the cells and expanded such that RNA-containing molecules—which have entered the cell and are nuclease-resistant—are selected. The method, therefore, selects nuclease-resistant RNA-containing molecules that have been internalized into the cell. In particular embodiments, the RNAs function to internalize compounds into cells in the absence of other delivery materials, such as cationic lipids, liposomes, or electroporation.

In another aspect, a method is provided for the selection of internalizable RNA-containing molecules. The method entails contacting a cell (e.g., a eukaryotic cell) or protaryotic with a random library of RNA-containing molecules. The cells that are contacted with the random library are exposed to one or more nucleases. Total RNA is extracted from the cells and expanded such that the extracted RNA-containing molecules are expanded.

In some embodiments, the selection method is repeated using the RNA-containing molecules identified from one round of selection. In other embodiments, an internalized RNA-containing molecule is selected using two or more rounds of the selection method. In certain embodiments, an internalized RNA-containing molecule is selected using at least ten rounds of the selection method. In certain embodiments, the internalizable RNA-containing molecules are exposed to the cell for decreasing lengths of time in each subsequent round of selection. In particular embodiments, the internalizable RNA-containing molecules are exposed to the cell for about 24 hours. In more particular embodiments, the internalizable RNA-containing molecules are exposed to the cell for less than 10 hours. In still further embodiments, the internalizable RNA-containing molecules are exposed to the cells for less than 5 hours. In still other embodiments, the internalizable RNA-containing molecules are exposed to the cells for less than 2 hours, less than 1 hour, less than 30 minutes, less than 20 minutes, less than 10 minutes, less than 5 minutes, less than 2 minutes, less than 1 minute, or less than 30 seconds.

In very particular embodiments, the method comprises isolating internalizable, RNA-containing molecules through multiple rounds of selection in which each subsequent round of selection entails exposing the internalizable RNA-containing molecule from a previous round of selection to the cells for a decreased length of time as compared to the previous round of selection. For example, the first round of selection includes exposing the internalizable RNA-containing molecules to the cells for 10 hours, the second round entails exposing the RNA-containing molecules selected from the first round to the cells for 5 hours, and then exposing the RNA-containing molecules selected in the second round to the cells for 2 hours, and so forth. Such a procedure identifies those compounds that most rapidly internalize into a cell-of-interest.

In other embodiments, the library contains functional RNA-containing molecules from a pool of randomized sequences. In certain embodiments, the RNAs each comprise at least one random sequence. In another embodiment, the RNA-containing molecules comprise at least one constant sequence. In more particular embodiments, the RNAs comprise two or more constant sequences.

In more embodiments, the random sequence comprises at least 10 nucleotides. In certain embodiments, the random sequence comprises at least 20 nucleotides. In more certain embodiments, the random sequence comprises at least 30 nucleotides. In particular embodiments, the random sequence comprises at least 40 nucleotides. In more particular embodiments, the random sequence comprises at least 50 nucleotides, 60 nucleotides, 70 nucleotides, 80 nucleotides, 90 nucleotides, or more than 100 nucleotides.

In more embodiments, the random library comprises stabilized RNAs. In certain embodiments, the stabilized RNAs are 2'-fluoro-modified RNA pools.

In one embodiment, the method comprises the step of determining the sequence of the internalized nucleic acids. In some embodiments, this step comprises direct sequencing, reverse transcriptase-polymerase chain reaction, binding to an array, mass spectrometry and combinations thereof.

In particular embodiments, the nucleases include RNase A, RNase B, RNase C, RNase 1, RNase T1, RNase T2, RNase L, RNase H, angiogenin RNase, eosinophil RNase, a micrococcal nuclease, a mammalian ribonuclease 1, a ribonuclease 2, a messenger RNA ribonuclease, 5'-3' exoribonuclease, 3'-5' exoribonuclease, a decapping enzyme, a deadenylase, RNase P, RNase III, RNase B, RNase I,I*, RNase HI, RNase HII, RNase M, RNase R, RNase IV, F; RNase P2,0, PIV, PC, RNase N, RNase II, PNPase, RNase D, RNase BN, RNase T, RNase PH, OligoRNase, RNase R, RNase Sa, RNase F1, RNase U2, RNase Ms, or RNase St and combinations thereof or commercially available nuclease cocktails. In another embodiment, the nuclease is a DNAse I, DNAse IIa or DNAse IIB.

In certain embodiments, specific nucleic acids are selected for internalization into cells expressing the CD4 receptor (e.g., HeLa). In other embodiments, the selected RNA-containing molecules are linked to siRNAs, toxins, miRNAs, small molecules and other molecules for delivery to CD4-expressing cells, such as HeLa cells.

In certain aspects, a selection scheme for RNA capable of internalizing into cells without the aid of conventional transfection or delivery mechanisms (e.g., cationic liposomes, electroporation, transfection reagents, etc.) has been developed. This scheme can be adapted to produce RNAs that internalize into specific cells, different states of cells, or to cells in general. The RNA-containing molecules can be selected to carry a variety of different cargos for therapeutic, diagnostic, or detection applications. This includes any number of techniques involving small molecule delivery into cells or labeling of cells including, but not limited to: gene expression modulation, such as siRNA knockdown studies; lethal drug delivery; FACS analysis; tumor detection; etc.

In other aspects, compositions and methods are provided for selecting internalizable RNA-containing molecules by contacting one or more cells with a random nucleic acid library which may contain constant sequence regions; washing the cells; exposing the cells to one or more nucleases; extracting total ribonucleic acids from the cells; and expanding the internalized ribonucleic acids, e.g., by reverse-transcription, polymerase chain reaction and transcription of the extracted nucleic acids, wherein each subsequent round of selection comprises contacting the cells with the expanded nucleic acid pool iteratively for decreasing lengths of time. The RNA-containing molecules can comprise RNA, DNA, modified RNA, or a chimeric nucleic acid. The molecules can also be at least partially nuclease resistant.

In one embodiment, a step of determining the sequence of the internalized nucleic acids is included. This step may comprise direct sequencing, reverse transcriptase-polymerase chain reaction, binding to an array, mass spectrometry and combinations thereof.

In certain embodiments, the nucleases used in this method are RNases or ribonucleases. In some embodiments, the nucleases include RNase A, RNase B, RNase C, RNase 1, RNase T1, RNase T2, RNase L, RNase H, angiogenin RNase, eosinophil RNase, a micrococcal nuclease, a mammalian ribonuclease 1, a ribonuclease 2, a messenger RNA ribonuclease, 5'-3' exoribonuclease, 3'-5' exoribonuclease, a decapping enzyme, a deadenylase, RNase P, RNase III, RNase B, RNase I,I*, RNase HI, RNase HII, RNase M, RNase R, RNase IV, F; RNase P2,0, PIV, PC, RNase N, RNase II, PNPase, RNase D, RNase BN, RNase T, RNase PH, OligoRNase, RNase R, RNase Sa, RNase F1, RNase U2, RNase Ms, or RNase St and combinations thereof or commercially available nuclease cocktails. In another embodiment, the nuclease is a DNAse I, DNAse IIa, DNAse IIB, or combinations thereof.

In another embodiment, the cells may be treated to prevent active endocytosis during the step of contacting the cells with the library. For ease of use and in certain embodiments, the nucleic acids are detectably labeled. In particular embodiments, the label is a dye or a fluorescent, radioactive or chemiluminescent label. Examples of detectable labels include one or more chromophores, an amplifiable nucleic acid sequence, an enzyme, a peptide, a metal, a magnetic bead, a polymeric bead, a dendrimer, a liposome, a quantum dot, a fluorescence resonance energy transfer molecule or another nucleic acid. In some embodiments, the cells are fixed prior to contact with the library of RNA-containing molecules.

In other embodiments, the RNA-containing molecules include or are linked to a second molecule, e.g., siRNAs, miRNAs, small molecules, toxins, or other molecules for delivery to a cell. In still other embodiments, the RNA-containing molecules are conjugated to a molecule targeted for internalization by hybridization, covalent conjugation, biotinylation, conjugation to streptavidin, non-specific binding, chelation, target-specific amino acid sequences, and combinations thereof.

In still more embodiments, the RNA-containing molecules are detectably labeled. In particular embodiments, the RNA-containing are operably linked to a detectable label such as chemiluminescent labels, radiolabels, or fluorescent labels. In certain embodiments, the RNA-containing molecule is identified by in vivo FISH, FACS, microarray, or microscopy. In other embodiments, nucleic acids are selected that do not enter the cell and remain in solution outside of the cell. In one embodiment, nucleic acids are selected that enter the cell and then re-emerge from the cell, e.g., via a cycling endocytotic pathway).

In another aspect, the methods also include the step of contacting one or more cells in a host organism, wherein host nucleases destroy nucleic acids not taken up by a target cell, organ, or compartment, and remaining nucleic acids are isolated. Cells for internalized nucleic acid selection are selected based on cellular or molecular phenotype, including cellular morphology, fluorescent protein expression, surface marker expression, or apoptosis.

In yet another aspect, a method is provided for selecting stabilized, internalizable, RNA-containing molecules comprising contacting one or more cells with a random library of RNA-containing molecules, comprising stabilized nucleic acids and constant sequence regions. The cells are washed and then exposed to one or more nucleases. Total ribonucleic acids are then extracted from the cells, and the internalized RNA-containing molecules are expanded. These selection steps are repeated, and each subsequent round of selection comprises contacting the cells with the expanded ribonucleic acid pool iteratively for decreasing lengths of time. In some embodiments, the RNA-containing molecules are expanded by RT-PCR.

In some embodiments, the RNA-containing molecules comprise RNA, DNA, modified RNA, or a chimeric nucleic acid. In certain embodiments, the RNA-containing molecules are at least partially nuclease resistant. In particular embodiments, the stabilized RNA-containing molecules comprise 2'-fluoro-modified nucleic acids. In some embodiments, the RNA-containing molecules are linked to siRNAs, miRNAs, small molecules, toxins, or aptamers. The nucleic acids of the RNA-containing molecules are detectably labeled in particular embodiments, such as with a fluorescent, radioactive or chemiluminescent label.

In some embodiments, the sequence of the RNA-containing molecules in the random sequence library comprise at least 10 nucleotides, at least 20 nucleotides, at least 30 nucleotides, at least 40 nucleotides, at least 50 nucleotides, at least 60 nucleotides, at least 70 nucleotides, at least 80 nucleotides, at least 90 nucleotides, or more than 100 nucleotides. In certain embodiments, the RNA-containing molecules comprise two or more constant sequences In some embodiments, the one or more nucleases are RNases or ribonucleases. In certain embodiments, the one or more nucleases are micrococcal nucleases, or are 5'-3' exoribonucleases, 3'-5' exoribonucleases, decapping enzymes, deadenylase, or combinations thereof. In other embodiments, the one or more nucleases is a DNAse, such as DNAse I, DNAse IIa, DNAse IIB, or combinations thereof. The one or more nucleases are mixed as a nuclease cocktail in particular embodiments.

In certain embodiments, the RNA-containing molecules are identified by in vivo FISH, FACS, microarray, or fluorescent microscopy. In some embodiments, the method further comprises the step of treating the cells to prevent active endocytosis. In addition, the sequence of the internalized nucleic acids can be determined in some embodiments of the method. In certain embodiments, sequencing is done by direct sequencing, reverse transcriptase-polymerase chain reaction, microarray, mass spectrometry, or combinations thereof. Furthermore, in some embodiments, the method further comprises the step of fixing the cells prior to contact with the nucleic acid library.

In another aspect, a kit for selecting internalizable, RNA-containing molecules is provided. The kit comprises a random nucleic acid library; one or more nucleases in an amount sufficient to degrade all non-internalized nucleic acids; a reverse-transcriptase, a DNA polymerase, or a RNA transcriptase; one or more buffers and instructions in accordance with the claimed methods of the invention. In certain embodiments, the nucleases are RNase A, RNase B, RNase C, RNase 1, RNase T1, RNase T2, RNase L, RNase H, an angiogenin RNase, eosinophil RNase, a micrococcal nuclease, a mammalian ribonuclease 1, a ribonuclease 2, a messenger RNA ribonuclease, 5'-3' exoribonuclease, 3'-5' exoribonuclease, a decapping enzyme, a deadenylase, RNase P, RNase III, RNase B, RNase I,I*, RNase HI, RNase HII, RNase M, RNase R, RNase IV, F; RNase P2,0, PIV, PC, RNase N, RNase II, PNPase, RNase D, RNase BN, RNase T, RNase PH, OligoRNase, RNase R, RNase Sa, RNase F1, RNase U2, RNase Ms, or RNase St.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

The patent and scientific literature referred to herein establishes knowledge that is available to those of skill in the art.

The issued US patents, allowed applications, published foreign applications, and references, including GenBank database sequences, that are cited herein are hereby incorporated by reference to the same extent as if each was specifically and individually indicated to be incorporated by reference. While the making and using of various embodiments of the present invention are discussed in detail below, it should be appreciated that many applicable concepts can be embodied in a wide variety of specific contexts. The specific embodiments discussed herein are merely illustrative of specific ways to make and use the invention and do not delimit the scope of the invention.

Compositions, methods and kits are included that allow for the rapid selection of isolated nucleic acids (DNA, RNA, and modifications thereof) without regard to sequence that are readily internalized into a particular type of cell. Once selected and isolated, the sequences of the RNA-containing molecules may be determined. The RNA-containing molecules can be used to enhance specific therapeutic molecule or drug delivery mechanisms to deposit specific compounds in cancer cells (e.g. for killing) or therapeutics for treating infections or other diseases associated with pathogen-damaged cells. The methods described herein are of great value for increasing product efficacy, or lowering toxicity.

Included herein are compositions and methods for selecting RNA-containing molecules capable of being internalized into cells without the aid of conventional transfection or delivery mechanisms. These methods are adapted to produce RNA-containing molecules that internalize into specific cells, different states of cells (e.g., differentiation) or to cells in general. Advantages of the present invention are that the RNA-containing molecules can be selected to be target-specific and, in some embodiments, have no associated toxicity. The internalizable RNA-containing molecules can be used to target a "payload" or "cargo" to a specific cell or tissue in some embodiments without the need to characterize the cells or the RNA-containing molecules to a great extent. The internalizable RNA-containing molecules can also be used to signal the internal state of the cell without compromising the structural integrity of the cell or tissue.

The term "gene" is used to refer to a functional protein, polypeptide or peptide-encoding unit. As used herein, "gene" is a functional term that includes genomic sequences, cDNA sequences or fragments or combinations thereof, as well as gene products, including those that may have been altered by the hand of man. Purified genes, nucleic acids, proteins and the like are used to refer to these entities when identified and separated from at least one contaminating nucleic acid or protein with which it is ordinarily associated. The term "sequences" as used herein is used to refer to nucleotides or amino acids, whether natural or artificial, e.g., modified nucleic acids or amino acids.

"Transcribed nucleic acids" refer to the ribonucleic acids produced from a corresponding nucleic acid sequence template. The term "gene" encompasses both cDNA and genomic forms of a gene. A gene may produce multiple RNA species that are generated by differential splicing of the primary RNA transcript.

As used herein, the term "expand" means to or amplify the amount or quantity of a target molecule in a sample. Target molecules include, but are not limited to, miRNA, siRNA, and double-strand RNA. Exemplary methods of amplification include PCR, RT-PCR, in vitro transcription, and standard cloning techniques.

As used herein, the term "amplify," when used in reference to nucleic acids, refers to the production of a large number of copies of a nucleic acid sequence by any method known in the art. The term "amplification" refers generally to reactions involving nucleic acid biomolecules, such as RNA and DNA. "Nucleic acid amplification" refers generally to any process of increasing the concentration of nucleic acid, and in particular, the concentration of a selected nucleic acid and/or a defined piece of a selected nucleic acid. "Amplified or amplification products" or "amplicons" generally define the products resulting from execution of a nucleic acid amplification reaction.

The terms "complementary" or "complementarity" as used herein, refer to the natural binding of polynucleotides under permissive salt and temperature conditions by base-pairing to other nucleic acids. For example, the sequence "A-G-T" binds to the complementary sequence "T-C-A". Complementarity between two single-stranded molecules may be partial, in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

As used herein, the term "internalizable" refers to a nucleic acid, such as a RNA-containing molecule, or modified nucleic acid that binds to a cell and has the ability to get into or be internalized into the cell without the aid of outside agents or conditions (e.g., calcium phosphate-DNA co-precipitation, DEAF-dextran-mediated transfection, polybrene-mediated transfection, electroporation, microinjection, liposome fusion, lipofection, protoplast fusion, retroviral infection, and biolistics). In some instances, the internalizable RNA-containing molecule has been internalized into a cell prior to detecting its internalization. In addition, internalizable nucleic acid can be used in conjunction with agents or conditions that increase the internalization rate after the original nucleic acids have been selected for internalization.

As used herein, the term "RNA-containing molecule" means a molecule that contains at least one portion of RNA or modified-RNA. RNA-containing molecules can be composed of multiple segments linked together. RNA-containing molecules can be attached to a cargo such as a nucleic acid, a polypeptide, a protein, a small molecule, a fatty acid, and/or an antibody. In certain embodiments, RNA-containing molecules are a single molecule having at least one RNA portion. In some embodiments, the RNA-containing molecule also contains an RNA cargo, such as siRNA or microRNA.

In certain embodiments, the RNA-containing molecule is attached to a cargo via a linkage, depending on the type of cargo. For example, such linkages can include dithiol linkages between the RNA and cargo such that upon entry into the reduced environment of the cell, the cargo and could be cleaved. Other useful linkages are phosphodiester linkages, phosphorothioate linkages, alkylphosphonates, phosphoramidites, carbamates, carbonates, phosphate esters, acetamide, and carboxymethyl esters (see, e.g., Agrawal et. al., (1987) *Tetrahedron Lett.* 28:3539-3542; Agrawal et. al., (1988) *PNAS (USA)* 85:7079-7083; Uhlmann et. al., (1990) *Chem. Rev.* 90:534-583; Agrawal et. al., (1992) *Trends Biotechnol.* 10:152-158).

The RNA-containing compounds can also be linked to cargoes via an HA peptide or similar compounds, or fusogenic peptides that would allow the cargoes break out of endosomes; or to photolytic elements that allow for cleavage of the cargoes from the RNA-containing compounds when exposed to a particular wavelength of light.

As used herein, the term "primer" refers to an oligonucleotide, whether occurring naturally, as in a purified restriction digest, or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer may be single stranded for maximum efficiency in amplification but may alternatively be double stranded. If double stranded, the primer is first treated to separate its strands before being used to prepare extension products. The primer must be sufficiently long to prime the synthesis of extension products in the presence of the inducing agent. The exact length of the primers will depend on many factors, including temperature, source of primer and the use of the method.

As used herein the terms "protein", "polypeptide" or "peptide" refer to compounds comprising amino acids joined via peptide bonds and are used interchangeably.

As used herein, a "random library" refers to a collection of oligonucleotides, such as RNA-containing molecules, that include different sequences. Each member of the library may be at least partly random, but may also have one or more common and/or known sequences or sequence regions. For example, the library may be completely random, random in part, random in certain portions of the nucleic acids, random as to length and/or single or double stranded. The random nucleic acid library may be made synthetically, combinatorially or come from natural sources.

As used herein, the term "detectable labels" refers to compounds and/or elements that can be detected due to their specific functional properties and/or chemical characteristics, the use of which allows the agent to which they are attached to be detected, and/or further quantified if desired such as an enzyme, an antibody, a linker, a radioisotope, an electron dense particle, a magnetic particle and/or a chromophore or combinations thereof, e.g., fluorescence resonance energy transfer (FRET). There are many types of detectable labels, including fluorescent labels, which are easily handled, inexpensive and nontoxic.

As used herein, the term "contacting" refers to exposing an oligonucleotide library with one or more targets, e.g., cells or tissues, for some length of time that leads to the internalization of some or all of the nucleic acids without the need for secondary agents or conditions.

As used herein, the terms "target cell" refer to any cell (e.g., eukaryotic or prokaryotic) to which the pool of nucleic acids is contacted for internalizing into a cell. As used herein internalization is defined by the function of the nucleic acid, namely, that the nucleic acid is internalizable and/or internalized without the need for a targeting vector, or any secondary agent or condition that facilitates nucleic acid entry into the target cell.

Compositions, methods and kits are provided for isolating and characterizing RNA-containing molecules that are target-specific and rapidly internalized. The compositions and methods disclosed herein allow for the rapid isolation of nucleic acids capable of internalizing into cells without the aid of conventional transfection or delivery mechanisms (e.g., cationic liposomes, electroporation, transfection reagents, etc). The method can be adapted to produce RNAs that internalize into specific cells, different states of cells, or to cells in general. The RNAs can be selected to carry a variety of different cargos for therapeutic, diagnostic or detection applications. This includes any number of techniques involving small molecule delivery into cells or labeling of cells including, but not limited to: gene expression modulation, such as siRNA knockdown studies; lethal drug delivery; FACS analysis; tumor detection; etc.

In particular embodiments, the cells contacted with the random library include cells isolated from tissues or cells propagated ex vivo (e.g., cell lines). In more particular embodiments, cells can be cancer cells including, but not limited to, lymphoma cells, melanoma cells, sarcoma cells, leukemia cells, retinoblastoma cells, hepatoma cells, myeloma cells, glioma cells, mesothelioma cells, and carcinoma cells.

In other embodiments, the cells can be cell lines. Exemplary cell lines include, but are not limited to, HeLa, MCF7, MDA, SKOV3, OVCAR3, 2008, PC3, T84, HCT-116, H69, H460, HeLa, and MOLT4. Cell lines can also be generated by techniques well known in the art (see, e.g., Griffin et. al., (1984) *Nature* 309(5963): 78-82).

Furthermore, the cells contacted with the random library include prokaryotic cells (i.e., bacterial cells). The method described herein can be used to identify RNA-containing molecules that deliver and internalize cargo (i.e., agents such as small molecules, antibodies, proteins, peptides, fatty acids, therapeutic agents, antibiotics or toxic agents) into the bacterial cells. The methods described herein can also be used to identify RNA-containing molecules that can deliver and internalize cargo into fungal cells.

In certain aspects, the methods provided herein allow for selecting internalizable RNA-containing molecules. Such RNA-containing molecules have the ability to internalize into cells and to bring cargo (e.g., drugs, cytotoxic agents, apoptotic agents) into the selected cells. The methods include contacting cells with a random library of RNA-containing molecules, which can be modified to increase stability.

The contacted cells can be washed with a denaturing agent to remove excess RNA-containing molecules adhering to the surface of the cells. Useful washes include denaturing agents such as anionic detergents such as sodium dodecyl sulfate (SDS), non-ionic detergents such as Tween-20®, and cationic detergents such as hexadecyltrimethylammonium bromide, all of which are commercially available (Sigma Corp., St. Louis, Mo.).

It has been discovered that nucleases can be used to remove RNA-containing molecules that have not been internalized. This result was surprising considering that RNA-containing molecules are generally stabilized against degradation due to modifications described more fully below and secondary structures. Due to this discovery, certain embodiments of the method entail exposing random library contacted cells to a nuclease or mixture of nucleases to remove RNA-containing molecules that remain on the surface of the cells and have not internalized into the cells. Examples of nucleases include, but are not limited to, RNase A, RNase B, RNase C, RNase 1, RNase T1, RNase T2, RNase L, RNase H, angiogenin RNase, eosinophil RNase, a micrococcal nuclease, a mammalian ribonuclease 1, a ribonuclease 2, a messenger RNA ribonuclease, 5'-3' exoribonuclease, 3'-5' exoribonuclease, a decapping enzyme, a deadenylase, RNase P, RNase III, RNase B, RNase I,I*, RNase HI, RNase HII, RNase M, RNase R, RNase IV, F; RNase P2,0, PIV, PC, RNase N, RNase II, PNPase, RNase D, RNase BN, RNase T, RNase PH, OligoRNase, RNase R, RNase Sa, RNase F1, RNase U2, RNase Ms, or RNase St and combinations thereof. In other embodiments, the nuclease is a DNAse I, DNAse IIa or DNAse IIB. In addition, RNase cocktails can be obtained commercially from Ambion Corp. (Austin, Tex.), New England BioLabs (Ipswich, Mass.), and Epicenter Technologies (Madison, Wis.).

In particular embodiments, the method is repeated multiple times to obtain those RNA-containing molecules that are the most rapidly internalized molecules as against the original pool of RNA-containing molecules. In these embodiments, a nucleic acid pool is added to cells and incubated with the cells for decreasing lengths of time over the course of the selection process (i.e., the method described above is performed repeatedly). After the time course is complete, the cells are washed several times and/or treated with a nucleasing step.

In certain embodiments, contacted cells can be incubated with RNA-containing molecules for decreasing lengths of time. A wash to remove RNA-containing molecules that have not been internalized can be performed between 1 hour and 24 hours, or longer, after the cells have been contacted with the RNA-containing molecules. Each succeeding wash can be performed at decreasing periods of time after the cells have been contacted by the RNA-containing molecules. Contacted cells can be incubated with RNA-containing molecules for any time period. Time periods include, but are not limited to, 1 minute to 10 minutes, 11 minutes to 20 minutes, 21 minutes to 30 minutes, 31 minutes to 40 minutes, 41 minutes to 50 minutes, 51 minutes to 1 hour, 1 hour to 2 hours, 2 hours to 3 hours, 3 hours to 4 hours, 4 hours to 5 hours, 5 hours to 6 hours, 6 hours, to 7 hours, 7 hours to 8 hours, 8 hours to 9 hours, 9 hours to 10 hours, 10 hours or longer, 15 hours or longer, 20 hours or longer, or 24 hours or longer.

In an exemplary embodiment, RNA-containing molecules are chosen by a first wash in which cells contacted with RNA-containing molecules are incubated for 24 hours. The contacted cells are washed and the internalized RNA-containing molecules are isolated, and contacted with cells for 1 hour. Those cells are washed and the internalized RNA-containing molecules are isolated. The isolated RNA-contacted molecules are contacted with cells for 30 minutes prior to being washed. The internalized RNA-containing molecules are again isolated, and the process continues with decreasing periods of incubation prior to washing.

In certain embodiments, total RNA is extracted from the cells, and any sequences that had been internalized can be recovered by RT-PCR and/or transcription. Those RNA-containing molecules represent the pool of molecules that most rapidly internalized into the cells.

RNA-containing molecules can be made using any procedures known in the art. For example, they can be synthetically produced using the Expedite™ Nucleic Acid Synthesizer (Applied Biosystems, Foster City, Calif.) or other similar devices (see, e.g., Applied Biosystems, Foster City, Calif.). Synthetic oligonucleotides also can be produced using methods well known in the art such as phosphoramidite methods (see, e.g., Pan et. al., (2004) *Biol. Proc. Online.* 6:257-262), H-phosphonate methodology (see, e.g., Agrawal et. al., (1987) *Tetrahedron Lett.* 28(31): 3539-3542) and phosphite trimester methods (*Nucleic Acids Res*. (1984), 12: 4539; (1983) *Tetrahedron Lett.* 24: 5843).

RNA-containing molecules can be attached to linkers such as 3' amino linkers or 5' amino linkers without changing the functionality of the RNA-containing molecules. Also, additional nucleotides can be attached to the 3' end of a RNA-containing molecules during nucleic acid synthesis for the purpose of acting as a linker (see, e.g., Steinberg et al., (2004) *Biopolymers* 73(5):597-605).

Additionally, the RNA-containing molecules can be modified in a number of ways that would not compromise their ability to internalize into a cell. Modifications to the nucleic acid structure can include synthetic linkages such as alkylphosphonates, phosphoramidites, carbamates, phosphorothioates, phosphorodithioates, carbonates, phosphate esters, acetamide, and carboxymethyl esters (see, e.g., Agrawal et. al., (1987) *Tetrahedron Lett.* 28:3539-3542; Agrawal et. al., (1988) *PNAS (USA)* 85:7079-7083; Uhlmann et. al., (1990) *Chem. Rev.* 90:534-583; Agrawal et. al., (1992) *Trends Biotechnol.* 10:152-158). Additionally, nucleic acid modifications include internucleoside phosphate linkages such as cholesteryl linkages or diamine compounds of varying numbers of carbon residues between the amino groups and terminal ribose. Other modifications of RNA-containing molecules include changes to the sugar moiety such as arabinose or 3', 5' substituted nucleic acids having a sugar attached at its 3' and 5' ends through a chemical group other than a hydroxyl group. Therefore, modifications that do not compromise the internalization or cargo delivery of the RNA-containing molecule are within the scope of the invention.

RNA-containing molecules can also be synthesized using standard solid-phase DNA chemistry, which is well known in the art. The following description shows one exemplary method of producing RNA pools. Randomized positions are generated by mixing the phosphoramidites for A, C, G and U at a molar ratio of 3:3:2:2.4 such that the coupling efficiency of each base is approximately equal, and the final composition of a random position has a 25% chance of being an A, C, G or U. In the case of doped pools, the mixture of phosphoramidites can be further used to generate additional pools of doped A, doped C doped G and doped U, such that each the coupling efficiency for any doped nucleotide is 70%, with a 10% efficiency for the remaining 3 nucleotide. For example, a doped A bottle would result in 70% A, 10% C, 10% G and 10% U. Following deprotection and purification steps, the single stranded DNA pools are converted to dsDNA by PCR or primer extension. During the process, a T7 promoter is appended to the 5' end of the pool making the resulting double stranded DNA a substrate for T7 RNA polymerase. RNA or modified RNA pools can then be generated by runoff transcription. Equivalent pools can also be purchased through such commercial sources as Invitrogen (Carlsbad, Calif.) or Integrated DNA Technologies (Coralville, Iowa).

In certain embodiments, RNA-containing molecules contain random regions. The random regions can be of any length that synthesis and purification will practically allow. In particular embodiments, the randomness can range from 10 random positions (N30) to over 100 random positions (N100). The RNA-containing molecules also contain constant regions that allow for PCR primers to bind and for transcription. For this reason, the ratio of random length to constant length will vary dependent on the length of the random region. That is, an N30 pool will have likely have nearly the same amount of fixed positions to random regions while an N100 pool will have more random positions relative to constant regions. In a few cases, constant regions were found after selection to participate in the functionality of the final selected species.

Pools of RNA-containing molecules can also be synthesized with varying degrees of randomness. "Doped" pools are made by partially randomizing the positions of an already extant sequence. For example, the selection of a sequence that would bind HIV reverse transcriptase (RT) would require obtaining the native substrate of RT, partially randomize the sequence, and selecting for sequences that bind to RT better than its native substrate.

In other embodiments, RNA-containing molecules are modified to increase stability. For instance, RNA-containing molecules can be modified to 2'-fluoro modifications on all pyrimidine residues to increase stability against alkaline degradation and naturally occurring nucleases. Other base modifications are well known in the art.

For the methods described herein, variations can be introduced at several different points of the processes. The RNA-containing molecules can have different modifications such as 2'-fluoro-modified nucleotides, 2'-amino-modified nucleotides, 2'-O-methyl-modified RNAs, nucleic acids with peptide backbones, or combinations thereof. In addition, different nuclease solutions can be used and the nucleases can be incubated for differing lengths of time.

In a particular aspect, the RNA-containing molecules can be detectably labeled. As used herein, "detectably labeled" means that a RNA-containing molecule is operably linked to a moiety that is detectable. By "operably linked" is meant that the moiety is attached to the probe by either a covalent or non-covalent (e.g., ionic) bond. Methods for creating covalent bonds are known (see general protocols in, e.g., Wong, S. S., *Chemistry of Protein Conjugation and Cross-Linking*, CRC Press 1991; Burkhart et al., *The Chemistry and Application of Amino Crosslinking Agents or Aminoplasts*, John Wiley & Sons Inc., New York City, N.Y., 1999).

According to the invention, a "detectable label" is a moiety that can be sensed. Such labels can be, without limitation, fluorophores (e.g., fluorescein (FITC), phycoerythrin, rhodamine), chemical dyes, or compounds that are radioactive, chemoluminescent, magnetic, paramagnetic, promagnetic, or enzymes that yield a product that may be colored, chemoluminescent, or magnetic. The signal is detectable by any suitable means, including spectroscopic, photochemical, biochemical, immunochemical, electrical, optical or chemical means. In certain cases, the signal is detectable by two or more means. In certain embodiments, nucleic acid labels include fluorescent dyes, radiolabels, and chemiluminescent labels, which are examples that are not intended to limit the scope of the invention (see, e.g., Yu, et al., (1994) *Nucleic Acids Res.* 22(16): 3226-3232; Zhu, et al., (1994) *Nucleic Acids Res.* 22(16): 3418-3422).

For example, nucleotides of RNA-containing molecules can be conjugated to Cy5/Cy3 fluorescent dyes. These dyes are frequently used in the art (see, e.g., Yang et al., (2005) *Clin Cancer Res.* 11(2 Pt 1):612-20). The fluorescent labels can be selected from a variety of structural classes, including the non-limiting examples such as 1- and 2-aminonaphthalene, p,p' diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a, 4a-diaza-s-indacene dyes and fluorescent proteins (e.g., green fluorescent protein, phycobiliprotein).

Other useful dyes are chemiluminescent dyes and can include, without limitation, biotin conjugated RNA nucleotides. Labeling of RNAs can be accomplished by any means known in the art, e.g., CyScribe™ First Strand cDNA Labeling Kit (#RPN6200, Amersham Biosciences, Piscataway, N.J.).

RNA-containing molecules can be co-internalizing cargo by appending the cargo to the RNA-containing molecule. For instance, siRNA and other nucleic acid sequences can be directly synthesized onto the selected RNA, hybridized to the selected RNA, or chemically attached using procedures well known in the art. Exemplary cargoes include, but are not limited to, siRNA and microRNA.

In particular aspects, the RNA-containing molecule that internalizes cargo successfully in the cell is identified. In certain embodiments, the RNA-containing molecule is identified by functional analysis. For example, a RNA-containing molecule can deliver an siRNA that inhibits a particular pathway, which can be identified by observing a phenotype affected by the pathway. Alternatively, the level of expression of the siRNA target can be analyzed at the protein or RNA levels. Thus, this method is useful for delivery of cargo molecules to specific pathways in the cell.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error such as ±10%.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

EXAMPLES

This invention is further illustrated by the following examples, which should not be construed as limiting.

Example 1

1. Sequences and Primers.

The N30 pool used for these selections had the following sequence:

```
                                          (SEQ ID NO.: 1)
5'GGGAATGGATCCACATCTACGAATTCNNNNNNNNNNNNNNNNNNNNNNNN

NNNNNNNNTTCACTGCAGACTTGACGAAGCTT 3';
``` where N is any of the four bases. The pool was synthesized and purified as described below. Amplification primers for the N30 pool were as follows:
(forward) 41.30:

```
(forward) 41.30:
                                          (SEQ ID NO.: 2)
5'GATAATACGACTCACTATAGGGAATGGATCCACATCTACGA 3';

(reverse) 24.30:
```

```
                                          (SEQ ID NO.: 3)
5' AAGCTTCGTCAAGTCTGCAGTGAA 3';
```

The template for the anti-PSMA aptamer, A9, used in these assays had the following sequence:

```
                                          (SEQ ID NO.: 4)
5'GGGAGGACGAUGCGGACCGAAAAAGACCUGACUUCUAUACUAAGUCUA

CGUUCCCAGACGACUCGCCCGA 3',;
```

Amplification primers for A9 were as follows:

```
(forward)
                                          (SEQ ID NO.: 5)
5' TTCTAATACGACTCACTATAGGGAGGACGATGCGG 3';

(reverse)
                                          (SEQ ID NO.: 6)
5' TCGGGCGAGTCGTCTG 3';
```

All primers and the A9 template were ordered from IDT (Coralville, Iowa).

2. Pool Synthesis and Purification.

The pool used in this selection consisted of 30 random residues flanked by constant regions. The pool was synthesized on an ABI Expedite 8909 synthesizer (Foster City, Calif.). Randomized positions were generated by mixing the phosphoramidites for A, C, G and T at a molar ratio of 3:3:2:2.4 such that the coupling efficiency of each base is approximately equal, and the final composition of a random position has a 25% chance of being an A, C, G or T.

The solid phase resin of the synthesis was suspended in 1 mL of 30% $NH_4OH$ overnight at 55° C. to deprotect the DNA. The reaction was centrifuged to pellet the resin, and the $NH_4OH$ layer containing the DNA was precipitated in 10 mL n-butanol at 4° C. and 13,000 rpm for 45 min. The pellet was washed with 70% ethanol and then dried. Given that aborted synthesis products are often present in long sequences, the DNA was gel-purified on a 10% acrylamide/7M urea gel. The band corresponding to full-length product was excised from the gel, chopped into fragments and eluted overnight in $dH_2O$. The eluted DNA was precipitated in 100% ethanol with glycogen as a precipitation carrier, washed with 70% ethanol and dried.

Following deprotection and purification, the single stranded DNA pool was converted to dsDNA by extension and large scale PCR using the primers 41.30 and 24.30. The 41.30 primer also served to add a T7 promoter sequence to the pool for later transcription steps. Approximately 2.8 nmol single stranded pool DNA was mixed with 115 nmol 24.30 primer and 0.2 mM each nucleotide (dATP, dCTP, dGTP and dTTP, GE Healthcare, Piscataway, N.J.) in a total volume of 43 mL. The sample was denatured at 65° C. for 5 min and then chilled to 4° C. A master mix of 50 mM KCl, 100 mL Tris-Cl (pH=8.3), 1.5 mM $MgCl_2$, 1,440 U Taq polymerase (NEB, Ipswich, Mass.) in a total volume of 43.3 mL was added to the denatured pool and incubated at 72° for 1 hr. At the end of the extension, 115 nmol 41.30 in a total volume of 28.7 mL was added, and the reaction was cycled at 94° C. for 30 sec, 50° C. for 30 sec and 72° C. for 1 min for 8 to 9 cycles, followed by a 72° C. step for 2 min. PCR products were precipitated in 2.5× volumes 100% ethanol at 4° C. for 45 min followed by a 70% ethanol wash and then dried. A large scale transcription was performed to generate the starting Round 0 pool in which 75 µg pool PCR was added to a 1.5 mL transcription mix of 40 mM Tris (pH=8.0), 26 mM $MgCl_2$, 5 mM DTT, 5 mM ATP, 5 mM GTP, 5 mM 2'-fluoro-CTP, 2'-fluoro-UTP, 0.01 U pyrophosphatase and 75 U of Y639F T7 polymerase. The N30 pool was estimated to have a complexity of approximately $10^{15}$ sequences. This input amount would, therefore, represent about 1.5 genome's worth of sequences. This scale adequately accounts for each possible sequence synthesized and therefore, represented maximal diversity.

The transcription reaction was allowed to run overnight at 37° C. After incubation, 75 U of DNAse I (Epicentre, Madison, Wis.) was added to the reaction, and the reaction was further incubated for 30 min. An equal volume of 2× denaturing dye (7 M urea, 90 mM Trizma base, 90 mM boric acid, 0.5 mM EDTA and 0.1% bromophenol blue) was added, and the reaction was denatured at 70° C. for 3 min before gel purification, as described above.

3. Cell Lines and Culture.

HeLa-CD4 cells were obtained from the NIH AIDS Research & Reference Reagent Program (Germantown, Md.). LnCap cells were purchased through ATCC (Manassas, Va.). Both lines were maintained in RPMI-1640 (ATCC, Manassas, Va.) supplemented with 10% fbs (Invitrogen, Carlsbad, Calif.) and grown at 37° C. and 5% $CO_2$ atmosphere. For trypsinization, cells were washed once with 1 culture volume of DPBS, then 1/10 volume of 0.05% trypsin-EDTA (Invitrogen, Carlsbad, Calif.) was added to the cells. Cells were incubated at 37° C. for approximately 2 min until cells lifted off. The trypsin was inactivated by adding culture media. All cell washing steps used room temperature PBS. All cell centrifugation steps were at 4° C. and 1500 rpm for 5 min.

4. Nuclease Assays.

To ensure that the modified RNAs and cells could survive the digestion and selection protocol, the dsDNA pool was transcribed as described above in a scaled-down reaction. $\alpha$-$^{32}$P-labeled-GTP (Perkin Elmer, Shelton, Conn.) was included in the reaction to generate body-labeled radioactive transcripts.

For the assay, approximately $4\times10^6$ HeLa-CD4 cells were aliquoted into each tube, spun down at 1500 rpm at 4° C. for 5 min. After washing once with 500 μL PBS, each tube of cells was resuspended into 85 μL of RNA and incubated at room temperature for 15 min. Different amounts of Riboshredder or RNAse T1 were added and the cells were incubated for another 30 min. The cells were spun away and the recovered RNA was run on an 8% acrylamide gel with 1×TBE and 7 M urea. The gel was dried onto filter paper (Whatman, Florham Park, N.J.) and exposed overnight on a phosphorimager screen for scanning.

To determine that cells were not adversely affected by the washing, incubation or nucleasing steps, repeats of these nuclease digestion assays were done and cells were counted and aliquoted into separate tubes. At different intervals, cells from each of the tubes were mixed and counted again. No significant cell health issues were observed.

5. Internalization Assay.

Internalization assays were performed using a cell surface aptamer, the anti-PSMA aptamer, A9 (Lupold et al., (2002) Cancer Res. 62(14): 4029-33). A9 was transcribed from an oligo template using a scaled-down version of the pool transcription outlined above in "Pool synthesis and purification".

Three days prior to the assay, $1\times10^5$ LnCap cells were seeded into a 24-well plate. After the cells had settled, cells were washed and fresh media was added. After equilibrating for an hour at 37° C. and 5% $CO_2$, the cells were treated with one of four conditions. In the "RNA" sample, 50 nM A9 was added directly to media on cells for 45 min. In the "az-dG" sample, cells were first treated for 10 min with 10 mM sodium azide and 50 mM deoxyglucose to prevent endocytosis, then RNA was added to the media after washing with 250 μL DPBS. In the "Rb" sample, RNA was incubated on cells, and then cells were washed with 250 μL DPBS before nuclease treatment with 0.02 U/uL Riboshredder (Epicentre, Madison, Wis.) for 15 min to digest binders. Finally, in the "az-dG/Rb" sample, cells were treated with az-dG before adding RNA, and cells were nuclease treated after RNA digestion. Following addition of RNA, those samples treated with az-dG were also incubated on ice-cold blocks to arrest other internalization mechanisms. Each treatment was performed in triplicate.

After treatment, all samples were washed with 500 μL DPBS, and total cell RNA from each sample was extracted with Trizol (Invitrogen, Carlsbad, Calif.) using Phase Lock tubes according to manufacturer protocols (Eppendorf, Westbury, N.Y.). Quantitation of the RNAs showed similar amounts of recovered RNA (data not shown), suggesting that none of the treatments significantly varied in content. The total extracted RNA was reverse-transcribed with aptamer-specific primers in scaled-down reactions akin to those described in "Pool synthesis and purification" and assayed by real-time PCR.

For real-time PCR, 600 nM psma5 and psma3 was mixed with 12.5 μL 2× SybrMix and 10 μL of a 1:10 dilution of each of the RT reactions. The samples were loaded onto an ABI 7300 real time machine and cycled as follows: 95° C. for 10 min, followed by 40 cycles of 95° C. for 30 sec, 50° C. for 30 sec and 72° C. for 1 min. Following cycling, a dissociation step was included to check the integrity of products as follows: 95° C. for 15 sec, 60° C. for 30 sec and 95° for 15 sec. The ACT was determined by comparing the CT of each sample to a non-treated cell control.

6. Internalization Selection.

One day prior to a selection round, $4\times10^5$ HeLa-CD4 cells were plated onto two 60 mm tissue culture plates. One hour prior to each selection round, the culture media was replaced with fresh media. For the first round of selection, 54 μg of modified pool RNA (1.2 mM), representing approximately 1 genome's worth of the pool, was added to one of the two plates. After incubation for 3 days, the cells were trypsinized, washed twice with D-PBS (Invitrogen, Carlsbad, Calif.) and total cell RNA was extracted from both plates using 1 mL Trizol (Invitrogen, Carlsbad, Calif.) and Phase Lock tubes following the manufacturer's instructions (Eppendorf, Westbury, N.Y.).

The recovered total cell RNA was reverse transcribed as follows: a reaction containing 84 μg total extracted RNA and 10 μM 24.30 reverse primer in 1× RT buffer (Invitrogen, Carlsbad, Calif.) was denatured at 70° C. for 5 min and then slow cooled to room temperature. A master mix of 10 mM DTT, 1 mM each dNTP and 28 U Superscript III reverse transcriptase (Invitrogen, Carlsbad, Calif.) was added into the mix and incubated at 50° C. for 1 hr. Smaller scaled no-RT controls of both pool-exposed and non-exposed cells were also performed to confirm that any recovered product was input pool RNA and not cell artifact or carryover DNA template.

One half of the RT reaction was used to seed the large scale PCR for the next round. Each round's pool was regenerated as per the protocol outlined in "Pool synthesis and purification" with modifications to adjust for the lowered scale of nucleic acid each round. In later rounds, it was also discovered that the primer concentrations used in the original pool amplification was in gross excess, and the concentrations of PCR primers were reduced to 0.4 mM each primer.

The rounds of the selection were performed with increasingly less input RNA, shorter incubation times and more wash steps. The progress of the selection was determined by assessing the number of PCR cycles required before an amplification product could be seen. This is often directly correlated to the amount of input material—in this case, how much pool RNA was likely recovered during that round of selection. A drastic drop in cycle # was seen after Round 3 (the first round to significantly reduce the amount of pool put onto cells) and after Round 5 when a fresh stock of cells was used. After Round 9, the PCRs did not appear to improve in cycle number, and the selection was deemed finished.

Example 2

1. Identification of RNA-Containing Molecules.

An internalizing RNA sequence, the anti-PSMA aptamer, A9, was used to test the novel conditions disclosed herein, and to identify RNA-containing molecules and ensure survival of internalizers.

Figure 1:
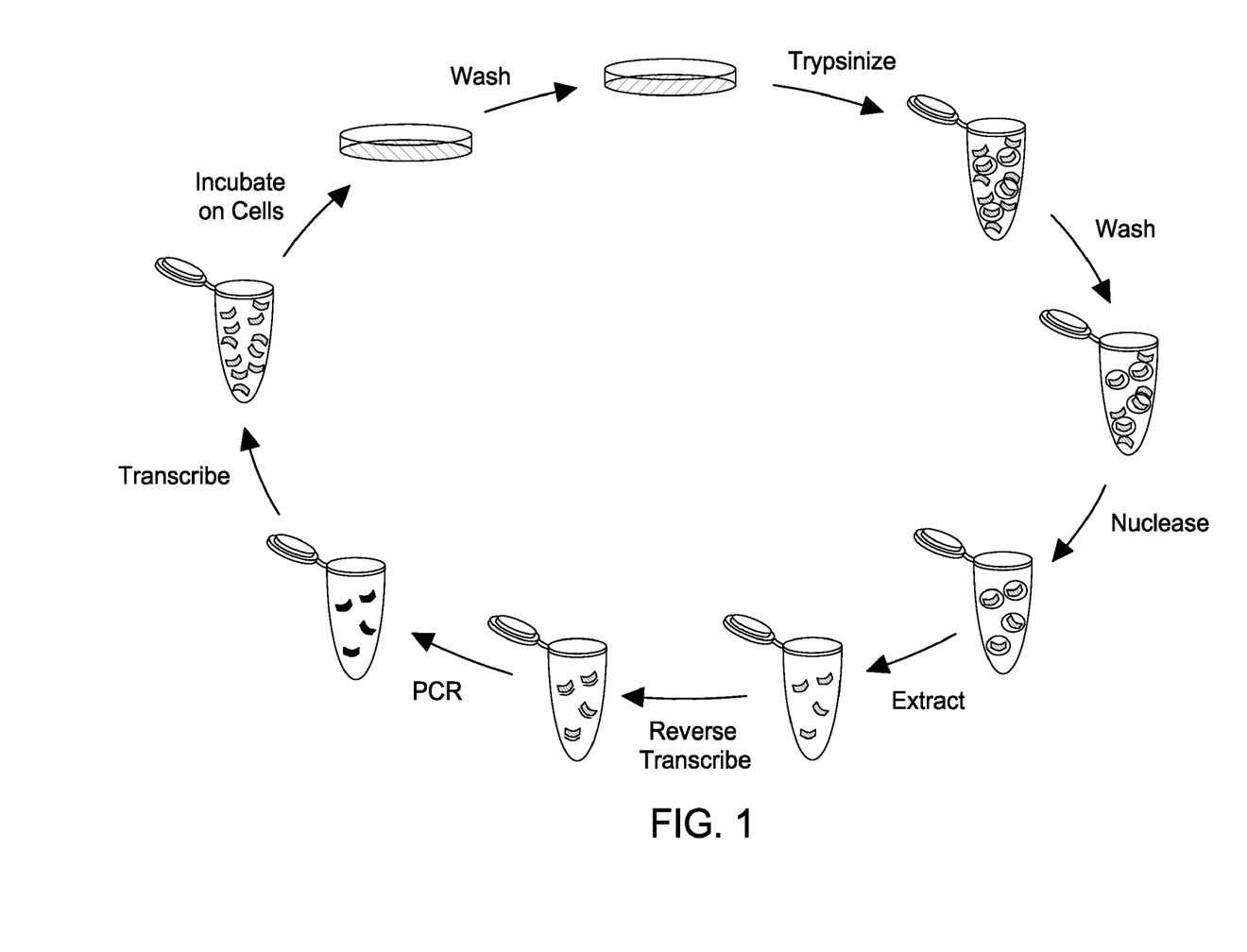
FIG. 1 shows a selection scheme for internalizing nucleic acids according to one embodiment.
Figure 2:
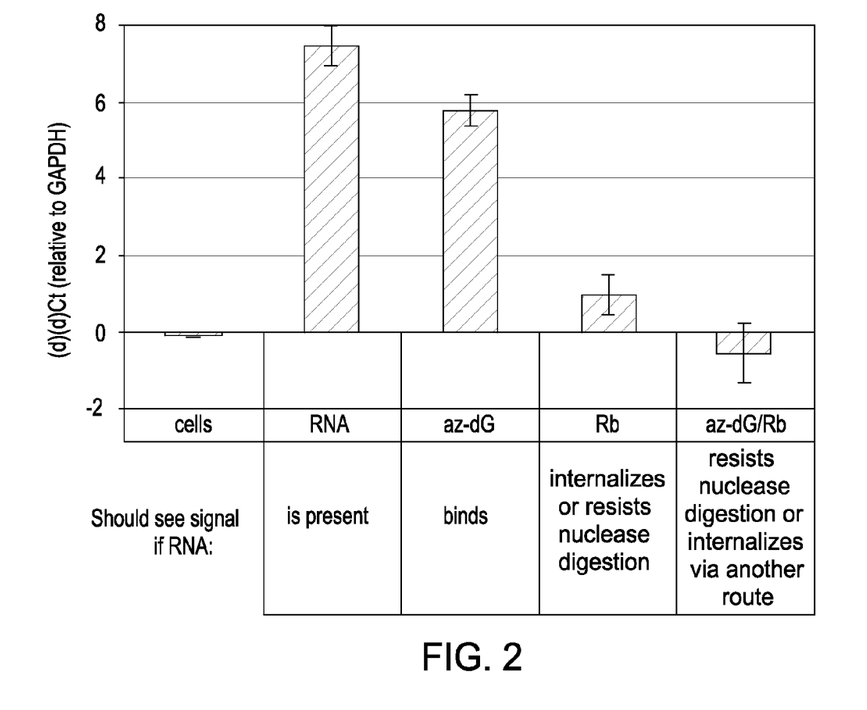
FIG. 2 is a graph that shows that the selection method enriches for internalizing RNAs.

FIG. 1 shows the effectiveness of the nucleasing conditions. Approximately $10^6$ LnCap cells were treated with one of four conditions: anti-PSMA aptamer was added directly to media on cells (RNA); cells were first treated for 10 minutes with 10 mM sodium azide and 50 mM deoxyglucose to prevent endocytosis, then RNA was added to the media after washing (az-dG); RNA was added to cells, and then cells were nuclease treated with 0.02 U/uL Riboshredder (Epicentre) to digest binders (Rb); or cells were treated with az-dG before adding RNA, and cells were nuclease treated after RNA digestion. Each treatment was done in triplicate. Total cell RNA from each of the treatments was reverse-transcribed with aptamer-specific primers, and real-time PCR cycles were determined relative to GAPDH levels. Treatment with az-dG reduced the deltaCT signal slightly, while treatment with Rb reduced the signal drastically, indicating that much of the aptamer remained extracellular, but some were being protected. Treatment with both az-dG and Rb abolished signal completely; the signal from the Rb treatment was due to internalized aptamer.

2. Selection.

A doped, 2'-fluoro-modified RNA pool based on the A9 aptamer, wherein each base position of the aptamer was doped by about 30%, was used to test the selection scheme proposed herein. Three to five micrograms of the doped PSMA pool was added to LnCap cells at 70-80% confluency in a T25 flask, and cells were incubated overnight. Cells were then washed with PBS and treated with 0.01 U/µL Riboshredder in PBS for 10 min. Cells were then washed three times and total cellular RNA was extracted with 1 mL Trizol. The recovered RNA was reverse transcribed and amplified via PCR to generate template for transcription of the next round.

Figure 3:
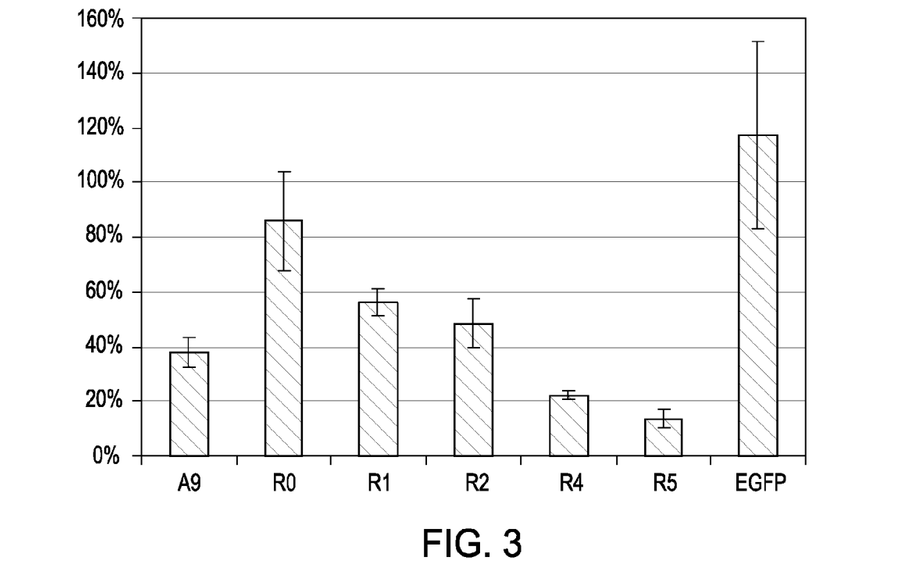
FIG. 3 is a graph that shows the progress of the doped PSMA rounds' ability to deliver lamin A/C siRNA conjugates into cells.
Figure 4:
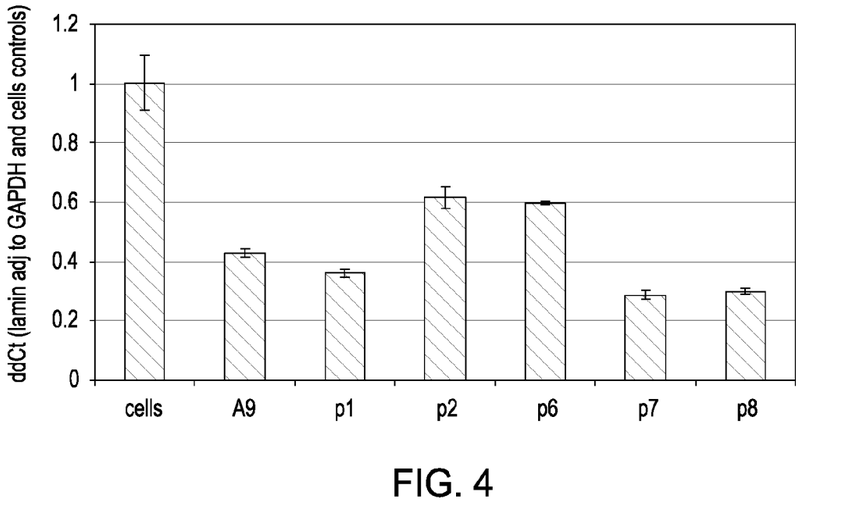
FIG. 4 is a graph that shows that doped PSMA aptamer clones effectively deliver lamin A/C siRNA conjugates into cells.

After five rounds of selection, the rounds were tested for their ability to internalize streptavidin/biotin conjugates loaded with anti-lamin A/C siRNA, as previously performed with the A9 aptamer itself (Chu et al., (2006) Nucleic Acids Res. 34(10): e73). An anti-eGFP siRNA served as a negative control (FIG. 3). Five clones of the Round 5 pool were amplified, sequenced and tested for internalization of the lamin A/C siRNA. All 5 clones (p1, p2, p6-8) demonstrated reduction of lamin A/C expression as normalized to GAPDH and cells control, indicating their ability to enter cells independent of any transfection methods. siRNA conjugates without A9 or the clones did not demonstrate lamin A/C knockdown. Three of the five clones (p1, p7, p8) showed slightly better knockdown of lamin A/C as compared to the wild-type A9 aptamer (FIG. 4).

Figure 5:
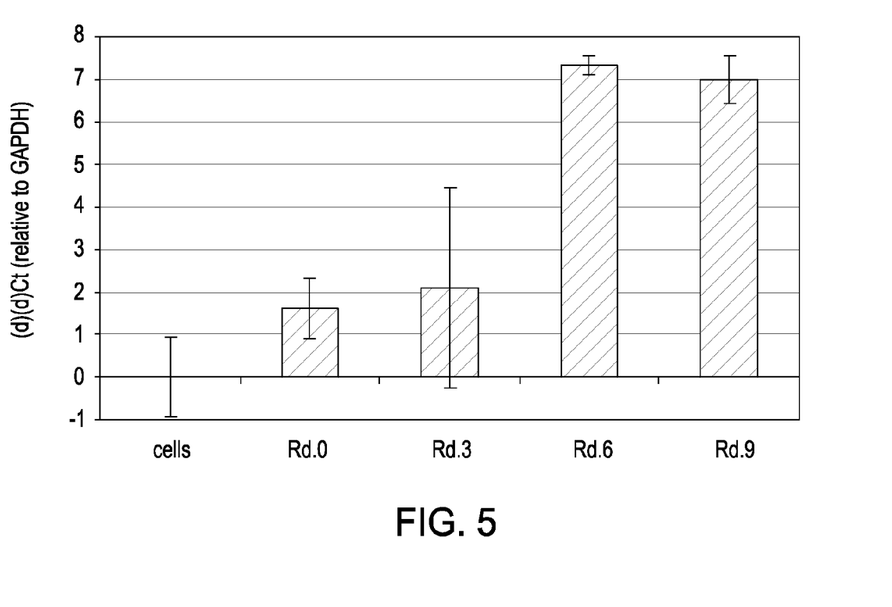
FIG. 5 is a graph that shows the progress of the N30 pool internalization selection on HeLa-CD4 cells.

Selections for internalizers from a random pool of nucleic acids. For the initial selection, a 2'-fluoro-modified RNA pool with a 30-base random region was used to select for sequences that would internalize into HeLa-CD4 cells. The nuclease step was not included in the first two rounds. For rounds 1-6, the RNA pool was incubated on cells for 1 day. Periodically, pool-treated cells were Trizol-extracted and the total RNA was reverse transcribed and amplified in real-time PCR reactions to check for the presence of pool RNA in cells. After Round 6, amplification signal appeared to peak (see FIG. 5). One more round was carried out with the 1 day incubation, then subsequent rounds were only incubated on cells for 1 hour. Round 9 did not improve significantly. Round 9 clones were isolated and tested for their ability to transport siRNA into cells. Table 1 Summarizes the various rounds of selection.

Table 1.

|  | Round | | | | | |
| --- | --- | --- | --- | --- | --- | --- |
|  | 1 | 2 | 3 | 4 | 5 | 6 |
| input RNA | 57.5 ug | 20 ug | 20 ug | 10 ug | 10 ug | 10 ug |
| incubation | 3 days | 1 day | 1 day | 1 day | 1 day | 1 day |
| RNAse | No | Yes | * | Yes | Yes | Yes |
| Cycles | 15 | 15 | 26 | 26 | 12 | 18 |

*Rds. 1 & 2 used more input in the PCRs

Example 3

1. Identification of RNA-Containing Molecules

An internalizing RNA sequence, the anti-PSMA aptamer, A9, is used to test the method of iteratively decreasing the length of time that cell are contacted with a RNA-containing molecule. The conditions and reagents are identical to those described above.

2. Selection

The selection conditions are substantially similar to those disclosed above. Briefly, a doped, 2'-fluoro-modified RNA pool based on the A9 aptamer, wherein each base position of the aptamer is doped by about 30%, is used to test the selection scheme proposed herein. Three to five micrograms of the doped PSMA pool is added to LnCap cells at 70-80% confluency in a T25 flask, and cells are incubated overnight. Cells are then washed with PBS and are treated with 0.01 U/µL Riboshredder in PBS for 10 min. Cells are washed three times and total cellular RNA is extracted with 1 mL Trizol. The recovered RNA is reverse transcribed and is amplified via PCR to generate template for transcription of the next round.

The recovered RNA is then incubated using the same procedure as above, with the exception that the incubation period is reduced to 12 hours. The RNA recovered from the second round of selection is incubated for 10 hours, with all other washes and conditions being identical to the first round. Round four has an incubation period of 8 hours, round five has a period of 4 hours, round six has a period of 2 hours, and rounds seven through nine have a period of 1 hour. After the first five rounds of selection, the rounds are tested for their ability to internalize streptavidin/biotin conjugates loaded with anti-lamin A/C siRNA, as previously performed with the A9 aptamer itself (Chu et al., (2006) Nucleic Acids Res. 34(10): e73). An anti-eGFP siRNA serves as a negative control. Clones of the Round 9 pool are amplified, are sequenced and are tested for internalization of the lamin A/C siRNA. Clones demonstrate reduction of lamin A/C expression, as normalized to GAPDH and control cells that are not exposed to the siRNA. This indicates their ability to enter cells independent of any transfection methods. siRNA conjugates without A9 or the clones do not demonstrate lamin A/C knockdown. Clones identified from later rounds of incubation also show faster internalization than clones identified in round 1, indicating that clones from later rounds of selection are more rapidly internalized.

EQUIVALENTS

Those skilled in the art will recognize, or be able to ascertain, using no more than routine experimentation, numerous equivalents to the specific compositions and procedures described herein. Such equivalents are considered to be within the scope of this invention, and are covered by the following claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for selecting RNA-containing molecules capable of being internalized, the method comprising:
   a) contacting a cell with a random library of RNA-containing molecules, wherein RNA-containing molecules capable of being internalized are internalized by the cell;
   b) exposing the contacted cells to one or more nucleases having RNase activity, wherein RNA-containing molecules that are not internalized by the cell are degraded by the nucleases;
   c) extracting total RNA from the contacted cells; and
   d) expanding the internalized RNA-containing molecules from the total RNA isolated from the cells,
in selecting for RNA-containing molecules capable of being internalized.

2. The method of claim 1, wherein the selection method is repeated using the RNA-containing molecules selected from a previous round of selection.

3. The method of claim 1, wherein the RNA-containing molecules capable of being internalized are selected for using two or more rounds of the selection method.

4. The method of claim 3, wherein the selected RNA-containing molecules are contacted with one or more cells for decreasing lengths of time in each subsequent round of selection.

5. The method of claim 1, wherein one or more cells are contacted with the RNA-containing molecules capable of being internalized for less than 24 hours, less than 10 hours, less than 5 hours, less than 2 hours, less than 1 hour, less than 30 minutes, less than 20 minutes, less than 10 minutes, less than 5 minutes, less than 2 minutes, less than 1 minute, or less than 30 seconds.

6. The method of claim 1, further comprising isolating the selected RNA-containing molecules through multiple rounds of selection in which each subsequent round of selection involves exposing the RNA-containing molecules selected from a previous round of selection to the cells for a decreased length of time as compared to the previous round of selection.

7. The method of claim 1, wherein the library contains functional RNAs from a pool of randomized sequences.

8. The method of claim 1, wherein the RNA-containing molecules capable of being internalized comprise at least one random sequence and at least one constant sequence.

9. The method of claim 1, wherein the RNA-containing molecules capable of being internalized comprise two or more constant sequences.

10. The method of claim 1, wherein the random library is defined further as RNA-containing molecules that comprise a random sequence of at least 10 nucleotides, at least 20 nucleotides, at least 30 nucleotides, at least 40 nucleotides, at least 50 nucleotides, at least 60 nucleotides, at least 70 nucleotides, at least 80 nucleotides, at least 90 nucleotides, or more than 100 nucleotides.

11. The method of claim 1, wherein the random library is defined further as comprising stabilized RNAs.

12. The method of claim 1, wherein the RNA-containing molecules capable of being internalized are selected for internalization into cells expressing the CD4 receptor.

13. The method of claim 1, further comprising the step of treating the cells to prevent active endocytosis.

14. The method of claim 1, wherein the RNA-containing molecules capable of being internalized are detectably labeled.

15. The method of claim 1, wherein the cells are fixed prior to contact with the library of RNA-containing molecules.

16. A method for selecting stabilized RNA-containing molecules capable of being internalized, comprising:
   a) contacting one or more cells with a random nucleic acid library of RNA-containing molecules, the RNA-containing molecules comprising stabilized nucleic acids and containing constant sequence regions;
   b) washing the cells;
   c) exposing the cells to one or more nucleases having RNase activity;
   d) extracting total ribonucleic acids from the cells;
   e) expanding the RNA-containing molecules from the total ribonucleic acids;
   in selecting for RNA-containing molecules capable of being internalized; and
   f) repeating selection steps a)-e),
   wherein each subsequent round of selection comprises contacting the cells with the expanded nucleic acid pool iteratively for decreasing lengths of time.

17. The method of claim 16, wherein the RNA-containing molecules each has at least a portion of the RNA-containing molecule that is nuclease resistant.

18. The method of claim 16, further comprising the step of treating the cells to prevent active endocytosis.

19. The method of claim 16, wherein the RNA-containing molecules are detectably labeled.

20. The method of claim 16, further comprising the step of fixing the cells prior to contact with the nucleic acid library.

21. The method of claim 16, wherein the RNA-containing molecules comprise two or more constant sequences.

22. The method of claim 16, wherein the random sequences of the RNA-containing molecules in the library comprise at least 10 nucleotides, at least 20 nucleotides, at least 30 nucleotides, at least 40 nucleotides, at least 50 nucleotides, at least 60 nucleotides, at least 70 nucleotides, at least 80 nucleotides, at least 90 nucleotides, or more than 100 nucleotides.

* * * * *